United States Patent
Kuzuhara et al.

(10) Patent No.: US 7,037,347 B2
(45) Date of Patent: May 2, 2006

(54) PRETREATMENT AGENTS FOR ACIDIC HAIR DYES

(75) Inventors: Akio Kuzuhara, Osaka (JP); Mitsuo Sano, Osaka (JP)

(73) Assignee: Mandom Corporation, Osaka (JP)

( * ) Notice: Subject to any disclaimer, the term of this patent is extended or adjusted under 35 U.S.C. 154(b) by 230 days.

(21) Appl. No.: 10/333,054

(22) PCT Filed: Jul. 12, 2001

(86) PCT No.: PCT/JP01/06033

§ 371 (c)(1),
(2), (4) Date: Jan. 16, 2003

(87) PCT Pub. No.: WO02/05768

PCT Pub. Date: Jan. 24, 2002

(65) Prior Publication Data

US 2004/0045099 A1    Mar. 11, 2004

(30) Foreign Application Priority Data

Jul. 17, 2000  (JP)  ............... 2000-216550
Dec. 8, 2000   (JP)  ............... 2000/374945

(51) Int. Cl.
*D06P 1/39* (2006.01)

(52) U.S. Cl. .............. 8/501; 8/542; 8/551; 8/552; 8/585; 132/202; 132/208

(58) Field of Classification Search ............. 8/551, 8/552, 554, 585, 542, 501; 132/202, 208
See application file for complete search history.

(56) References Cited

U.S. PATENT DOCUMENTS

| | | | |
|---|---|---|---|
| 3,973,901 A * | 8/1976 | Micchelli et al. | 8/425 |
| 3,980,091 A | 9/1976 | Dasher et al. | 132/7 |
| 4,381,259 A * | 4/1983 | Homma et al. | 510/122 |
| 4,895,722 A * | 1/1990 | Abe et al. | 424/70.14 |
| 5,338,540 A | 8/1994 | Lee et al. | 424/71 |

FOREIGN PATENT DOCUMENTS

| | | |
|---|---|---|
| EP | 1 206 236 B1 | 5/2002 |
| GB | 2057261 A | 4/1981 |
| JP | 56-92812 A | 7/1981 |
| JP | 61-20523 B2 | 5/1986 |
| JP | 1-275519 A | 11/1989 |
| JP | 6-13451 B2 | 2/1994 |
| JP | 06-316512 A | 11/1994 |
| JP | 8-53328 A | 2/1996 |
| JP | 10-291919 A | 11/1998 |

(Continued)

OTHER PUBLICATIONS

J. Woodard, J. Soc. Cosmet. Chem., vol. 23, Sep. 14, 1972, pp. 593-603.

*Primary Examiner*—Eisa Elhilo
(74) *Attorney, Agent, or Firm*—Birch, Stewart, Kolasch & Birch, LLP

(57) ABSTRACT

Pretreatment agents for hair colorings with acid dye comprising at least one cationic polymer selected from the group consisting of polymers having amino groups and polymers having quaternary ammonium groups. The pretreatment agents for hair colorings with acid dye are used for improving coloring ability and color fastness of hair colorings with acid dye.

4 Claims, 4 Drawing Sheets

FOREIGN PATENT DOCUMENTS

| | | |
|---|---|---|
| JP | 11-335243 A | 12/1999 |
| JP | 2000-169343 A | 6/2000 |
| JP | 2000-169344 A | 6/2000 |
| WO | WO 01/06994 A1 | 2/2001 |

* cited by examiner

US 7,037,347 B2

PRETREATMENT AGENTS FOR ACIDIC HAIR DYES

This application is the national phase under 35 U.S.C. § 371 of PCT International Application No. PCT/JP01/06033 which has an International filing date of Jul. 12, 2001, which designated the United States of America.

TECHNICAL FIELD

The present invention relates to a pretreatment agent for a hair coloring with acid dye. More specifically, the present invention relates to a pretreatment agent for a hair coloring with acid dye, which improves coloring ability and color fastness of the hair coloring with acid dye.

BACKGROUND ART

A hair coloring with acid dye has a defect such that the coloring ability is generally weaker than an oxidation hair dye. Therefore, in order to eliminate the defects, various attempts hitherto have been studied.

As a process for improving coloring ability, there has been known a method of adding benzyl alcohol, 2-benzyloxyethanol, urea, phenol, m-cresol or the like to an acidic water bath containing acid dye or the like, used in a solvent-assisted dyeing or a low-temperature dyeing in the case of wool dyeing ("*Senyoku no Kiso Butsurikagaku*," authored by Mitsuo Kimura, Sennikenkyusha, p. 51–54). Among the above-mentioned components added, benzyl alcohol has been generally widely used as a penetration agent for the acid dye. However, when this method is applied to a hair coloring with acid dye, there are some defects in this process such that coloring ability and color fastness of the hair coloring with acid dye become worse than those of the oxidation hair dye.

Also, as another process for improving coloring ability, there has been proposed to use 2-benzyloxyethanol (Japanese Patent Laid-Open No. Hei 4-69323). However, there are some defects in this process such that coloring ability and color fastness are equivalent to or lower than those of the above-mentioned benzyl alcohol.

Also, as one of low-temperature dyeing processes of keratin fibers such as wool or human hair, there have been proposed a process comprising previously treating keratin fibers with an amphoteric surfactant, and thereafter dyeing the keratin fibers (Japanese Patent Laid-Open No. Hei 2-502740); the above process using a cationic surfactant in place of the amphoteric surfactant (Japanese Patent Laid-Open No. Hei 8-301738); and the like. However, there are some defects in these processes such that coloring ability is not improved, and that coloring ability especially for damaged hair is rather worsened when combined with a commercially available hair coloring with acid dye.

Incidentally, as a component for improving luster, smooth combing, feeling and the like, there has been proposed to use cationic polymers. Among them, since polyethyleneimine is alkaline, there have been proposed to use the polyethyleneimine in a hair color containing an acid dye in place of an alkalizing agent such as ammonia or monoethanolamine (Japanese Examined Patent Publication No. Hei 6-13451); a hair dye composed of a first agent comprising polyethyleneimine and a second agent comprising a melanine precursor such as tyrosine or DL-β-alanine and a metal salt (Japanese Examined Patent Publication No. Sho 61-20523); and the like.

The cationic polymer has been used not only as an agent for improving luster, smooth combing and feeling as described above, but also as a dyeing assistance for improving coloring ability. However, there has not yet been reported a case where a cationic polymer is employed in acid dye.

As the reasons therefor, there can be cited that the acidic dye has a sulfo group in the molecule, so that an ion complex is formed between the sulfo group of acid dye and cationic group when the cationic polymer exists in acid dye, whereby the acid dye cannot be efficiently penetrated into the human hair, and therefore an alkaline cationic polymer such as polyethyleneimine cannot be mixed with acid dye.

From these reasons, it has been hitherto thought that simultaneous use of the cationic polymer and acid dye would be difficult.

DISCLOSURE OF INVENTION

In view of the above-mentioned prior art, an object of the present invention is to provide a means for further improving coloring ability and color fastness of a hair coloring with acid dye.

Another object of this invention is to provide a pretreatment agent for a hair dye, which is excellent not only in decoloring ability but also in coloring ability and color fastness when dyed with a hair coloring with acid dye after removing dye from colored hair, which gives no squeakiness during rinsing, and adequately keeps hair feeling.

According to this invention, there is provided a pretreatment agent for a hair coloring with acid dye comprising at least one cationic polymer selected from the group consisting of a polymer having amino groups and a polymer having quaternary ammonium groups.

BEST MODE FOR CARRYING OUT THE INVENTION

Figure 1:
FIG. 1 is a cross-sectional microphotograph (magnification: 400) of colored hair obtained in Example 21 of this invention.

As described above, the pretreatment agent for a hair coloring with acid dye of this invention contains at least one cationic polymer selected from the group consisting of a polymer having amino groups and a polymer having quaternary ammonium groups.

Since a specific cationic polymer is contained in the pretreatment agent for a hair coloring with acid dye of this invention as mentioned above, cation is introduced into hair when hair is treated with the pretreatment agent before coloring the hair with a hair coloring with acid dye. Therefore, there are exhibited excellent effects such that not only coloring ability and color fastness of a hair coloring with acid dye are improved, but also squeakiness is reduced when rinsing hair. Also, the same excellent effects as mentioned above are exhibited not only for virgin hair but also for damaged hair.

The polymer having amino groups includes, for instance, primary amine polymers such as polyacrylamide, polyvinylamine, polyethyleneimine (hereinafter referred to as PEI) and their derivatives; secondary amine polymers such as polyamine, PEI and their derivatives; tertiary amine polymers such as PEI and their derivatives; and the like. These cationic polymers can be used alone or in admixture of at least two kinds. Since PEI and its derivatives have a primary amino group, a secondary amino group and a tertiary amino group, they can be used as any one of primary amine polymer, secondary amine polymer and tertiary amine polymer.

Among these polymers having amino groups, PEI and its derivatives have a high density of electric charges and many cation charges in the molecule, PEI and its derivatives can be suitably used.

The derivative of PEI includes, for instance, a PEI derivative in which polyoxyethylene, polyoxypropylene, polyoxybutylene or an alkyl group having a molecular chain of 4 to 22 carbon atoms is added to secondary amino group or tertiary ethyleneimino group of PEI in an amount of equimolar or greater.

It is desired that the number-average molecular weight of PEI or its derivatives is 300 to 500000, preferably 300 to 300000, more preferably 500 to 100000.

Commercially available products of PEI include, for instance, EPOMIN SP-003, EPOMIN SP-006, EPOMIN SP-200, EPOMIN P-1000 [hereinabove manufactured by NIPPON SHOKUBAI CO., LTD., trade name], Lupasol [manufactured by BASF, trade name], and the like.

In addition, the polymer having quaternary ammonium groups includes, for instance, hydroxyethylcellulose-hydroxypropyltrimethylammonium chloride ether, hydroxyethylcellulose-dimethyldiallylammonium chloride copolymers, guar gum-hydroxypropyltrimetylammonium chloride ether, cationized pullulan, dimethyldiallylammonium chloride-acrylamide copolymers, vinylpyrrolidone diethylsulfate-N,N-dimethylaminoethyl methacrylate copolymers, dimethyldiallylammonium chloride homopolymers, dimethyldiallylammonium chloride-acrylic acid copolymers, acrylamide-acrylic acid-dimethyldiallylammonium chloride copolymers, cationized silicone copolymers and the like. These cation polymers can be used alone or in admixture of at least two kinds.

Commercially available products of the hydroxyethylcellulose-hydroxypropyltrimethylammonium chloride ether include, for instance, LEOGUARD G, LEOGUARD NGP, LEOGUARD KGP [hereinabove manufactured by LION CORPORATION, trade names], CATINAL HC-10, CATINAL LC-100 [hereinabove manufactured by Toho Chemical Industry Co., Ltd., trade names], and the like. Commercially available products of the hydroxyethylcellulose-dimethyldiallylammonium chloride copolymers include, for instance, CELQUAT L-200, CELQUAT H-60 [hereinabove manufactured by National Starch and Chemical Corp., trade names], and the like. Commercially available products of the guar gum-hydroxypropyltrimetylammonium chloride ether include, for instance, JAGUAR C-13-S, JAGUAR C-15-S [hereinabove manufactured by Sellanies Stein Hall, trade names], and the like. Commercially available products of the dimethyldiallylammonium chloride-acrylamide copolymers include, for instance, MERQUAT L-550 [manufactured by CALGON Corp., trade name], and the like. Commercially available products of the vinylpyrrolidone diethylsulfate-N,N-dimethylaminoethyl methacrylate copolymers include, for instance, H. C. Polymer 5 [manufactured by Osaka Organic Chemical Ind., Ltd., trade name, trade name], GAFQUAT 755N [manufactured by ISP, trade name], and the like. Commercially available products of the dimethyldiallylammonium chloride homopolymers include, for instance, MERQUAT 100 [manufactured by CALGON Corp., trade name], and the like. Commercially available products of the dimethyldiallylammonium chloride-acrylic acid copolymers include, for instance, MERQUAT 280, MERQUAT 295 [hereinabove manufactured by CALGON Corp., trade names], and the like. Commercially available products of the acrylamide-acrylic acid-dimethyldiallylammonium chloride copolymers include, for instance, MERQUAT PLUS 3330 [manufactured by CALGON Corp., trade name], and the like. Commercially available products of the cationized silicone polymer include SM8704C [manufactured by Toray-Dow Corning Silicone, trade name] and the like.

It is desired that the content of the cationic polymer in the pretreatment agent for a hair coloring with acid dye of this invention is 0.01 to 30% by weight, preferably 0.05 to 20% by weight, from the viewpoints of effectiveness of coloring ability and color fastness, reducing squeakiness during rinsing and economics (when the cationic polymer is added in an amount exceeding 30% by weight, the exceeding amount would be washed away by rinsing).

In addition, in the pretreatment agent for a hair coloring with acid dye of this invention, urea can be contained as a component other than the cationic polymer in order to further improve coloring ability and color fastness and reduce squeakiness during rinsing.

It is desired that the content of urea in the pretreatment agent for a hair coloring with acid dye of this invention is 0.1 to 60% by weight, preferably 0.5 to 40% by weight, from the viewpoints of effectiveness of coloring ability and color fastness, reducing squeakiness during rinsing and economics (when urea is added in an amount exceeding 60% by weight, the exceeding amount would be washed away by rinsing).

Also, in the present invention, it is preferable to use an organic solvent in order to accelerate the penetration of the cationic polymer into the hair.

The organic solvent includes, for instance, N-alkylpyrrolidones such as 1-methyl-2-pyrrolidone and 1-ethyl-2-pyrrolidone; lower alkylene carbonates such as ethylene carbonate and propylene carbonate; aromatic alcohols such as benzyl alcohol and 2-benzyloxyethanol; and the like. Furthermore, it is more preferable to use the above-mentioned aromatic alcohol in combination with the lower alcohol.

It is desired that the content of the organic solvent in the pretreatment agent for a hair coloring with acid dye of the present invention is 1 to 40% by weight, preferably 5 to 20% by weight, from the viewpoint of acceleration of satisfactory penetration of active ingredients into the hair. This is because when the content is less than 1% by weight, the effect of acceleration of satisfactory penetration of active ingredients into the hair would be insufficient, and when the content exceeds 40% by weight, no further effects can be desired.

The balance of the above-mentioned components in the pretreatment agent for a hair coloring with acid dye of this invention is water. As water, there can be used distilled water, tap water, purified water or the like.

It is desired that pH of the pretreatment agent for a hair coloring with acid dye of this invention is 2 to 11, preferably 7 to 11. pH can be easily adjusted by using a pH adjusting agent, including an organic acid such as citric acid, acetic acid, glycolic acid, levulinic acid or tartaric acid, phosphate buffer, ammonia, monoethanolamine, and the like.

The formulation of the pretreatment agent for a hair coloring with acid dye of this invention is not limited to specified ones. Examples of the formulation include, for instance, aqueous solution, cream, gel, dispersion, emulsion, aerosol, and the like.

The pretreatment agent for a hair coloring with acid dye of this invention can be used as follows. First, hair is dipped in the pretreatment agent for a hair coloring with acid dye of this invention at a temperature of room temperature to 60° C. for 1 minute to 1 hour, then washed with water, and thereafter dyed with a hair coloring with acid dye.

The hair coloring with acid dye is not limited to specified ones, and any of conventionally used ones can be used.

When the pretreatment agent for a hair coloring with acid dye of which pH is adjusted to 7 to 11 is used, since hair becomes alkaline, it is preferable to pre-treat the hair with a treatment agent so that the pH of the hair becomes around neutrality.

Furthermore, when the color of the colored hair with a hair coloring with acid dye is changed or when the hair is further dyed with a hair coloring with acid dye, cation would be introduced into the hair by the pretreatment agent if the hair is previously subjected to decoloring treatment with the pretreatment agent of this invention. Therefore, there are exhibited some excellent effects such that not only coloring ability and color fastness are improved by the hair coloring with acid dye, but also squeakiness during shampoo-rinsing of the hair is reduced. Such excellent effects can be also exhibited for damaged hair.

Thus, when the removal of dye from colored hair is carried out using the pretreatment agent of this invention, the removal of dye from colored hair can be effectively carried out. Furthermore, when the hair is colored again with a hair coloring with acid dye after removing dye from the colored hair, there are exhibited some excellent effects such that the hair is excellent in coloring ability and color fastness and shows no squeakiness during rinsing, and feeling of the hair is adequately maintained. Such effects would be maintained without lowering even when removing dye from colored hair using the pretreatment agent and coloring with the hair coloring with acid dye are repeatedly carried out. Therefore, coloring with the hair coloring with acid dye and removing dye from colored hair with the pretreatment agent can be repeatedly carried out.

EXAMPLES

Next, this invention will be more specifically described on the basis of the following examples, without intending to limit this invention thereto.

Examples 1 to 5 and Comparative Example 1

A component shown in Table 1 was diluted with distilled water so as to have a concentration as shown in Table 1, to obtain a pretreatment agent for a hair coloring with acid dye.

Coloring ability, color fastness and squeakiness were evaluated by the following methods using the obtained pretreatment agent for a hair coloring with acid dye. The results are shown in Table 1.

[Coloring Ability]

One gram of a bundle of dried yak hair was dipped in the pretreatment agent for a hair coloring with acid dye at room temperature for 15 minutes (liquor ratio: 15 times), and washed in water for 1 minute. Thereafter, the moisture contained in the bundle was wiped off with a KIMTOWEL.

Next, the bundle of yak hair treated above was dipped in a 0.1% by weight aqueous solution of Orange 205 at room temperature for 20 minutes (liquor ratio: 15 times), washed in water for 1 minute and sufficiently dried, to obtain a colored bundle of hair.

The colored bundle thus obtained was directly measured using a spectrocolorimeter (manufactured by Nippon Denshoku Kogyo K.K., trade name: SZ-Σ80, hereinafter referred to the same), and a color difference (ΔE) between the colored bundle and the uncolored bundle was calculated. Thereafter, the coloring ability was evaluated.

It is indicated that the larger the ΔE is, the better the coloring ability becomes.

[Color Fastness and Squeakiness]

Each bundle of colored hair was dipped in a 10% by weight aqueous solution of EMAL 20C (sodium polyoxyethylene lauryl ether sulfate(3E.O.), manufactured by Kao Corporation, trade name) at 40° C. for 3 hours (liquor ratio: 15 times), washed in water for 1 minute, and dried at room temperature. The dried bundle of colored hair was measured using the spectrocolorimeter, and a color difference (ΔE)

between the colored bundle of hair and the uncolored bundle of hair was calculated. The color fastness was evaluated by comparing this color difference with the color difference ($\Delta E$) calculated when the coloring ability was evaluated.

[Squeakiness when Washing Bundle of Hair with Water]

Five specialist panelists performed sensory evaluation on a decrease in squeakiness when the bundle of hair was washed in water on the basis of the following evaluation criteria.

(Evaluation Criteria)

⊚: Highly excellent (Four out of five evaluated as excellent).

○: Excellent (Three out of five evaluated as excellent).

Δ: Slightly wrong (Two out of five evaluated as excellent).

X: Wrong (At most one out of five evaluated as excellent).

Examples 6 to 9 and Comparative Example 2

PEIs having various molecular weights as shown in Table 2 were diluted with distilled water so as to have a concentration as shown in Table 2, to obtain a pretreatment agent for a hair coloring with acid dye.

Next, coloring ability was evaluated by the following method using the obtained pretreatment agent for a hair coloring with acid dye. The results are shown in Table 2.

[Coloring Ability]

One gram of a bundle of dried yak hair was dipped in the pretreatment agent for a hair coloring with acid dye at room temperature for 20 minutes (liquor ratio: 15 times), and washed in water for 1 minute. Thereafter, the moisture contained in the bundle was wiped off with a KIMTOWEL.

TABLE 1

| Ex. No. | Components of Pretreatment Agent for Acidic Hair Dye (% by weight) | | Coloring Ability ($\Delta E$) | Color Fastness ($\Delta E$) | Squeakiness |
|---|---|---|---|---|---|
| 1 | CELQUAT L200*[1] (5) | Distilled Water (95) | 39.8 | 35.3 | ○ |
| 2 | H. C. Polymer 5*[2] (5) | Distilled Water (95) | 39.6 | 33.6 | ○ |
| 3 | MERQUAT 100*[3] (5) | Distilled Water (95) | 41.9 | 35.1 | ○ |
| 4 | SP-200*[4] (5) | Distilled Water (95) | 42.6 | 32.4 | ⊚ |
| 5 | SP-006*[5] (5) | Distilled Water (95) | 43.2 | 37.9 | ⊚ |
| Comp. Ex. 1 | Distilled Water (100) | | 38.7 | 28.2 | X |

(Note)
*[1]Hydroxyethyl cellulose-dimethyldiallylammonium chloride copolymer (manufactured by National Starch and Chemical Corp., trade name: CELQUAT L200, molecular weight: 100000 to 140000)
*[2]Vinylpyrrolidone diethylsulfate-N,N-dimethylaminoethyl methacrylate copolymer (Osaka Organic Chemical Ind., Ltd., trade name: H. C. Polymer 5, molecular weight: 200000 to 300000)
*[3]Dimethyldiallylammonium chloride homopolymer (CALGON Corp., trade name: MERQUAT 100, molecular weight: 150000)
*[4]Polyethyleneimine (number-average molecular weight: 10000, manufactured by NIPPON SHOKUBAI CO., LTD., trade name: SP-200)
*[5]Polyethyleneimine (number-average molecular weight: 600, manufactured by NIPPON SHOKUBAI CO., LTD., trade name: SP-006)

It can be seen from the results shown in Table 1 that the hair treated with a pretreatment agent for a hair coloring with acid dye containing the polymer having amino groups or the polymer having quaternary ammonium groups (Examples 1 to 5) is more excellent in coloring ability and color fastness than the hair treated with distilled water obtained in Comparative Example 1.

Especially, it can be seen that coloring ability becomes more excellent when the hair is treated with the pretreatment agent for a hair coloring with acid dye containing PEI.

Also, when the hair is treated with the pretreatment agents for a hair coloring with acid dye obtained in Examples 1 to 5, it can be seen that there is no squeakiness during shampoo-rinsing, so that smooth hair treatment can be carried out.

Next, the bundle of yak hair treated above was dipped in a 0.1% by weight aqueous solution of Orange 205 (containing 4% by weight citric acid) at room temperature for 20 minutes (liquor ratio: 15 times), washed in water for 1 minute and sufficiently dried, to obtain a colored bundle of hair.

The colored bundle of hair thus obtained was directly measured using the spectrocolorimeter. The coloring ability was evaluated by calculating a color difference ($\Delta E$) between the colored bundle of hair and the uncolored bundle of hair.

It is indicated that the larger the $\Delta E$ is, the better the coloring ability becomes.

TABLE 2

| Ex. No. | Components of Pretreatment Agent for Acidic Hair Dye (% by weight) | | | Physical Properties Coloring Ability ($\Delta E$) |
|---|---|---|---|---|
| 6 | PEI [Number-Average Molecular Weight: 600] (10) | MP(5) | Distilled Water (85) | 46.9 |
| 7 | PEI [Number-Average Molecular Weight: 1800] (10) | MP(5) | Distilled Water (85) | 45.8 |

TABLE 2-continued

| | Components of Pretreatment Agent for Acidic Hair Dye (% by weight) | | | Physical Properties Coloring Ability ($\Delta E$) |
|---|---|---|---|---|
| 8 | PEI [Number-Average Molecular Weight: 10000] (10) | MP(5) | Distilled Water (85) | 48.3 |
| 9 | PEI [Number-Average Molecular Weight: 70000] (10) | MP(5) | Distilled Water (85) | 46.8 |
| Comp. Ex. 2 | — | MP(5) | Distilled Water (95) | 43.4 |

It can be seen from the results shown in Table 2 that the hair treated with a pretreatment agent for a hair coloring with acid dye containing PEI having a number-average molecular weight of 600 to 70000 (Examples 6 to 9) is more excellent in coloring ability than the hair treated with distilled water obtained in Comparative Example 2.

Examples 10 to 20 and Comparative Examples 3 and 4

PEI, urea and 1-methyl-2-pyrrolidone were dissolved in distilled water so as to have the contents as shown in Table 3, to obtain a pretreatment agent for a hair coloring with acid dye.

Next, coloring ability, color fastness and squeakiness were evaluated using the obtained pretreatment agent for a hair coloring with acid dye. The results are shown in Table 3.

Coloring ability was evaluated in accordance with the following method, and color fastness and squeakiness were evaluated in the same way as in Examples 1 to 5.

[Coloring Ability]

One gram of a bundle of dried yak hair was dipped in the pretreatment agent for a hair coloring with acid dye at 50° C. for 15 minutes (liquor ratio: 15 times), and washed in water for 1 minute. Thereafter, the moisture contained in the bundle was wiped off with a KIMTOWEL.

Next, the bundle of yak hair treated above was dipped in a 0.1% by weight aqueous solution of Orange 205 (containing 4% by weight citric acid) at room temperature for 20 minutes (liquor ratio: 15 times), washed in water for 1 minute and sufficiently dried, to obtain a colored bundle of hair.

The colored bundle thus obtained was directly measured using the spectrocolorimeter, and a color difference ($\Delta E$) between the colored bundle of hair and the uncolored bundle of hair is calculated. Thereafter, the coloring ability was evaluated.

It is indicated that the larger the $\Delta E$ is, the better the coloring ability becomes.

TABLE 3

| | Components of Pretreatment Agent for Acidic Hair Dye (% by weight) | | | | Physical Properties | | |
|---|---|---|---|---|---|---|---|
| Ex. No. | SP-006 | Urea | MP | Distilled Water | Coloring Ability ($\Delta E$) | Color Fastness ($\Delta E$) | Squeakiness |
| 10 | 0.10 | 0 | 5 | 94.9 | 44.4 | 38.0 | ◯ |
| 11 | 1.25 | 0 | 5 | 93.75 | 44.3 | 37.0 | ◯ |
| 12 | 2.50 | 0 | 5 | 92.5 | 44.9 | 38.5 | ◯ |
| 13 | 5.00 | 0 | 5 | 90.0 | 44.6 | 39.8 | ◯ |
| 14 | 10.0 | 0 | 5 | 85.0 | 44.9 | 38.5 | ◯ |
| 15 | 20.0 | 0 | 5 | 75.0 | 43.5 | 39.3 | ◯ |
| 16 | 10.0 | 0.5 | 5 | 84.5 | 44.7 | 40.4 | ◎ |
| 17 | 10.0 | 5.0 | 5 | 80.0 | 46.7 | 43.3 | ◎ |
| 18 | 10.0 | 10.0 | 5 | 75.0 | 44.4 | 40.4 | ◎ |
| 19 | 10.0 | 20.0 | 5 | 65.0 | 44.8 | 41.6 | ◎ |
| 20 | 10.0 | 40.0 | 5 | 45.0 | 46.3 | 42.9 | ◎ |
| Comp. Ex. | | | | | | | |
| 3 | 0 | 0 | 5 | 95.0 | 40.9 | 33.8 | X |
| 4 | 0 | 20.0 | 5 | 75.0 | 41.9 | 35.0 | X |

(Note)
SP-006: Polyethyleneimine (manufactured by NIPPON SHOKUBAI CO., LTD., trade name, molecular weight: 600)
MP: 1-Methyl-2-pyrrolidone It can be seen from the results shown in Table 3 that the hair treated with a pretreatment agent for a hair coloring with acid dye containing 0.10 to 20% by weight of PEI (Examples 10 to 20) is more excellent in coloring ability and color fastness than the hair treated with a pretreatment agent obtained in Comparative Example 3, in which PEI is not used.

Also, it can be seen that the pretreatment agents for a hair coloring with acid dye containing urea (Examples 16 to 20) are more excellent in color fastness than the pretreatment agent for a hair coloring with acid dye not containing PEI (Example 14), and do not show squeakiness during rinsing.

In addition, it can be seen from the comparison of Example 19 with Example 14 and Comparative Example 4 that the combined use of PEI and urea more improves coloring ability and color fastness as synergistic effects than the single use of PEI or the single use of urea.

Examples 21 to 24 and Comparative Examples 5 and 6

PEI, urea and 1-methyl-2-pyrrolidone were dissolved in distilled water so as to have a content as shown in Table 4, to obtain a pretreatment agent for a hair coloring with acid dye.

Next, coloring ability, color fastness and squeakiness were evaluated using the obtained pretreatment agent for a hair coloring with acid dye. The results are shown in Table 4.

Coloring ability was evaluated in accordance with the following method, and color fastness and squeakiness were evaluated in the same way as in Examples 1 to 5.

[Coloring Ability]

One gram of a bundle of dried white human hair was dipped in the pretreatment agent for a hair coloring with acid dye at 50° C. for 15 minutes (liquor ratio: 15 times), and washed in water for 1 minute. Thereafter, the moisture contained in the bundle was then wiped off with a KIM-TOWEL.

Next, the bundle of white human hair treated above was dipped in a 0.1% by weight aqueous solution of Orange 205 (containing 4% by weight citric acid) at 50° C. for 20 minutes (liquor ratio: 15 times), washed in water for 1 minute and sufficiently dried, to obtain a colored bundle of hair.

The colored bundle thus obtained was directly measured using the spectrocolorimeter, and a color difference ($\Delta E$) between the colored bundle of hair and the uncolored bundle of hair is calculated. Thereafter, the coloring ability was evaluated.

Figure 5:
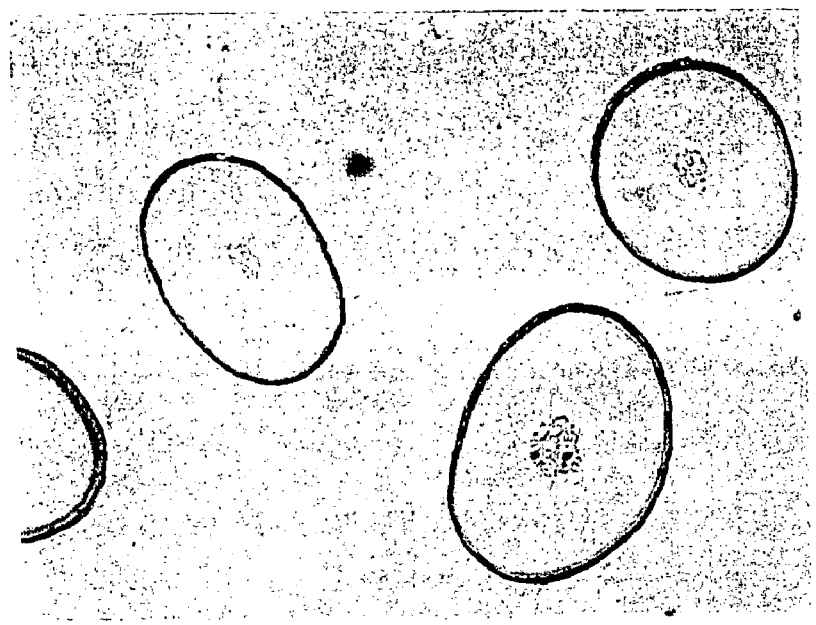
FIG. 5 is a cross-sectional microphotograph (magnification: 400) of colored hair obtained in Comparative Example 5.

It is indicated that the larger the $\Delta E$ is, the better the coloring ability becomes.

coloring ability and color fastness than the pretreatment agent not containing PEI obtained in Comparative Example 5 (FIG. 5) because the pretreatment agents for hair colorings with acid dye containing PEI accelerate the penetration of the dye.

Figure 2:
FIG. 2 is a cross-sectional microphotograph (magnification: 400) of colored hair obtained in Example 22 of this invention.

Also, it can be seen that the pretreatment agents for a hair coloring with acid dye in which PEI and urea are used together (Examples 23 and 24, FIGS. 3 and 4) is more excellent in coloring ability and color fastness and show no squeakiness during rinsing because the penetration of the dye is more accelerated than the pretreatment agents for a hair coloring with acid dye in which PEI is singly used (Examples 21 and 22, FIGS. 1 and 2).

Figure 3:
FIG. 3 is a cross-sectional microphotograph (magnification: 400) of colored hair obtained in Example 23 of this invention.
Figure 4:
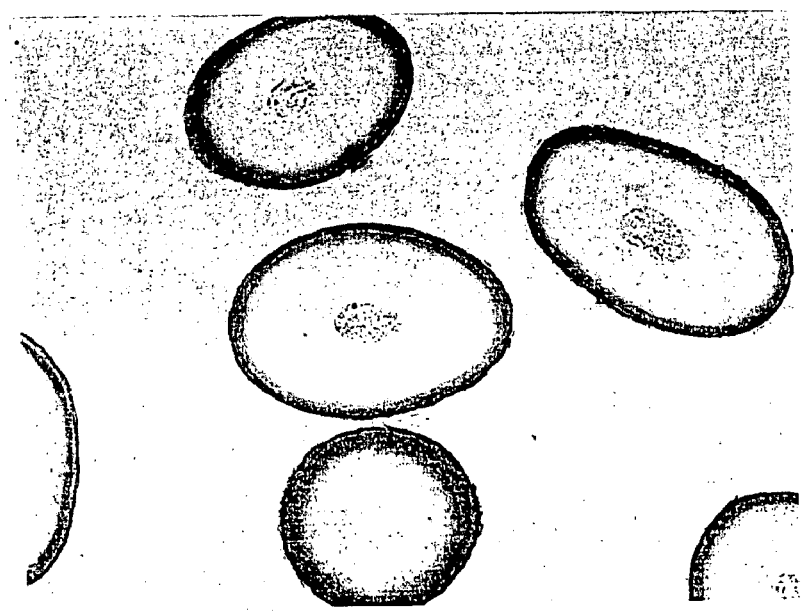
FIG. 4 is a cross-sectional microphotograph (magnification: 400) of colored hair obtained in Example 24 of this invention.
Figure 6:
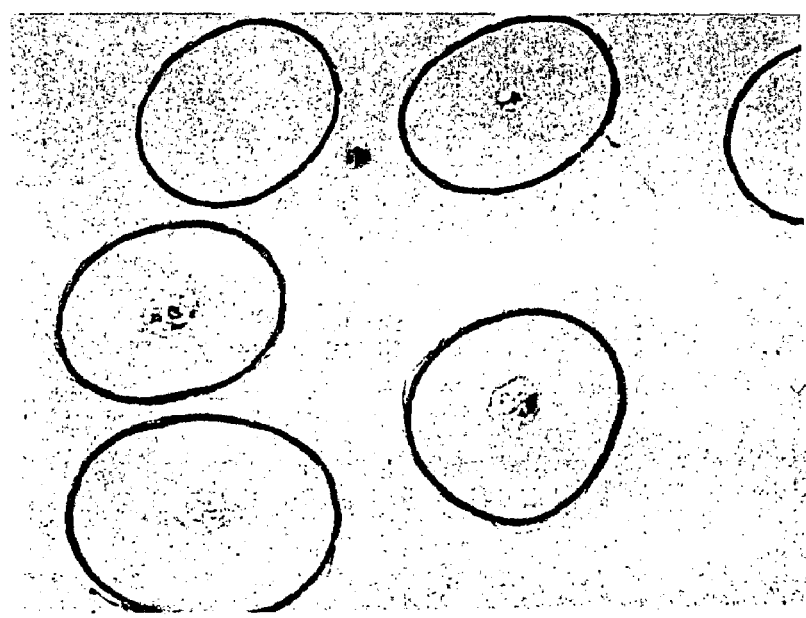
FIG. 6 is a cross-sectional microphotograph (magnification: 400) of colored hair obtained in Comparative Example 6.

In addition, it can be seen that the pretreatment agent for a hair coloring with acid dye containing not PEI but urea obtained in Comparative Example 6 (FIG. 6) does not so improve coloring ability and color fastness. To the contrary, the pretreatment agents for hair colorings with acid dye containing both urea and PEI obtained in Examples 23 and 24 are excellent in coloring ability and color fastness and show no squeakiness during rinsing (FIGS. 3 and 4).

Examples 25 and 26 and Comparative Examples 7 to 9

PEI, QUARTAMIN 86W, urea and 1-methyl-2-pyrrolidone were dissolved in distilled water so as to have contents as shown in Table 5, to obtain a pretreatment agent for a hair coloring with acid dye.

Next, coloring ability, color fastness and squeakiness were evaluated using the obtained pretreatment agent for a hair coloring with acid dye. The results are shown in Table 5.

Coloring ability was evaluated in accordance with the following method, and color fastness and squeakiness were evaluated in the same way as in Examples 1 to 5.

[Coloring Ability]

One gram of a bundle of dried white human hair was dipped in the pretreatment agent for a hair coloring with acid

TABLE 4

| | Pretreatment Agent for Acidic Hair Dye (% by weight) | | | | | Physical Properties | | |
|---|---|---|---|---|---|---|---|---|
| | SP-006 | SP-200 | Urea | MP | Distilled Water | Coloring Ability ($\Delta E$) | Color Fastness ($\Delta E$) | Squeakiness |
| Ex. No. | | | | | | | | |
| 21 | 10 | — | 0 | 5 | 85 | 52.0 | 48.3 | ○ |
| 22 | — | 10 | 0 | 5 | 85 | 54.2 | 50.6 | ○ |
| 23 | 10 | — | 20 | 5 | 65 | 52.4 | 48.6 | ◎ |
| 24 | — | 10 | 20 | 5 | 65 | 56.7 | 55.1 | ◎ |
| Comp. Ex. | | | | | | | | |
| 5 | 0 | 0 | 0 | 5 | 95 | 51.2 | 41.7 | X |
| 6 | 0 | 0 | 20 | 5 | 75 | 52.4 | 43.8 | X |

(Note)
SP-006: Polyethyleneimine (manufactured by NIPPON SHOKUBAI CO., LTD., trade name, molecular weight: 600)
SP-200: Polyethyleneimine (manufactured by NIPPON SHOKUBAI CO., LTD., trade name, molecular weight: 10000)
MP: 1-Methyl-2-pyrrolidone It can be seen from the results shown in Table 4 that the pretreatment agents for hair colorings with acid dye containing PEI (Examples 21 to 24) are more excellent in dye at 50° C. for 15 minutes (liquor ratio: 15 times), and washed in water for 1 minute. Thereafter, the moisture contained in the bundle was wiped off with a KIMTOWEL.

Next, the bundle of white human hair treated above was dipped in a 0.1% by weight aqueous solution of Orange 205 (containing 4% by weight citric acid) at 50° C. for 20 minutes (liquor ratio: 15 times), washed in water for 1 minute and sufficiently dried, to obtain a colored bundle of hair.

The colored bundle thus obtained was directly measured using the spectrocolorimeter, and a color difference (ΔE) between the colored bundle of hair and the uncolored bundle of hair is calculated. Thereafter, the coloring ability was evaluated.

It is indicated that the larger the ΔE is, the better the coloring ability becomes.

Examples 27 to 30 and Comparative Examples 10 to 13

PEI, QUARTAMIN 86W, urea and 1-methyl-2-pyrrolidone were dissolved in distilled water so as to have contents as shown in Table 6, to obtain pretreatment agents for a hair coloring with acid dye.

Next, coloring ability, color fastness and squeakiness were evaluated using the obtained pretreatment agents for hair colorings with acid dye. The results are shown in Table 6.

Coloring ability was evaluated in accordance with the following method, and color fastness and squeakiness were evaluated in the same way as in Examples 1 to 5.

TABLE 5

| | Pretreatment Agent for Acidic Hair Dye | | | | | Physical Properties | | |
|---|---|---|---|---|---|---|---|---|
| | (% by weight) | | | | | Coloring | Color | |
| | P-1000 | QUARTAMINE 86W | Urea | MP | Distilled Water | Ability (ΔE) | Fastness (ΔE) | Squeakiness |
| Ex. No. | | | | | | | | |
| 25 | 10 | 0 | 0 | 5 | 85 | 55.5 | 47.5 | ○ |
| 26 | 10 | 0 | 20 | 5 | 65 | 54.3 | 53.1 | ◎ |
| Comp. Ex. | | | | | | | | |
| 7 | 0 | 0 | 0 | 5 | 95 | 52.8 | 42.1 | X |
| 8 | 0 | 5 | 0 | 5 | 90 | 56.9 | 51.6 | X |
| 9 | 0 | 5 | 20 | 5 | 70 | 55.6 | 51.7 | X |

Figure 7:
FIG. 7 is a cross-sectional microphotograph (magnification: 400) of colored hair obtained in Example 25 of this invention.

(Note)
P-1000: Polyethyleneimine (manufactured by NIPPON SHOKUBAI CO., LTD., trade name, molecular weight: 70000)
QUARTAMIN 86W: Stearyltrimethylammonium chloride (manufactured by Kao Corporation, trade name, molecular weight: 348.1)
MP: 1-Methyl-2-pyrrolidone It can be seen from the results shown in Table 5 that the pretreatment agent for a hair coloring with acid dye containing PEI having a molecular weight of 70000 (Example 25, FIG. 7) is more excellent in coloring ability and color fastness than the pretreatment agent for a hair coloring with acid dye which does not contain PEI (Comparative Example 7).

Also, it can be seen that the pretreatment agents for hair colorings with acid dye containing stearyltrimethylammonium chloride (cationic surfactant having a low molecular weight) in place of PEI (Comparative Examples 8 and 9) somewhat improve coloring ability and color fastness, as compared to the pretreatment agent for a hair coloring with acid dye containing PEI having a molecular weight of 70000 (Example 25). However, the pretreatment agents show squeakiness.

Figure 8:
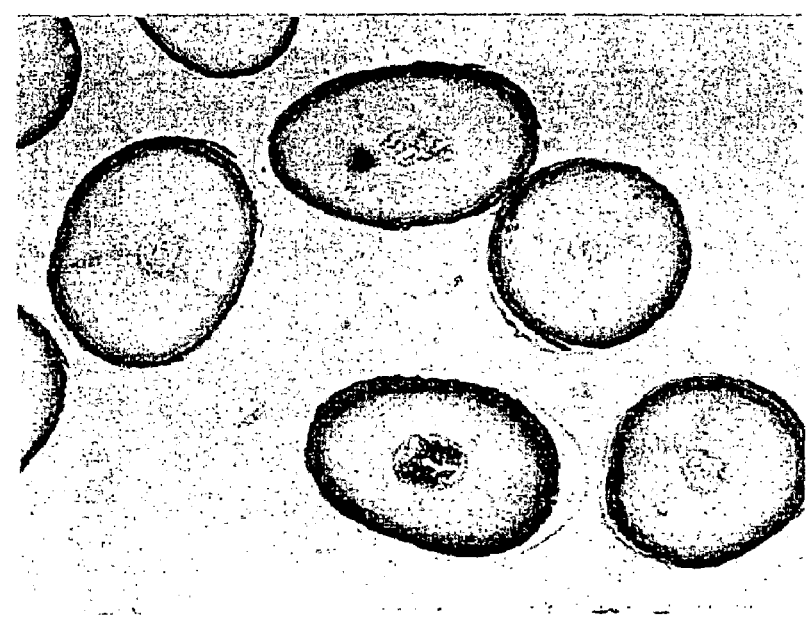
FIG. 8 is a cross-sectional microphotograph (magnification: 400) of colored hair obtained in Example 26 of this invention.

In addition, it can be seen that the pretreatment agent for a hair coloring with acid dye containing PEI having a molecular weight of 70000 and urea (Example 26, FIG. 8) is more excellent in color fastness and squeakiness than the pretreatment agent for a hair coloring with acid dye containing only stearyltrimethylammonium chloride (cationic surfactant having a low molecular weight) (Comparative Example 8).

[Coloring Ability]

One gram of a bundle of dried white human hair was subjected to bleaching treatment (6% aqueous hydrogen peroxide (pH 10.2), room temperature, 1 hr (liquor ratio: 1:50)) to previously obtain a bundle of damaged hair. One gram of the bundle of damaged hair was dipped in the pretreatment agent for a hair coloring with acid dye at 50° C. for 15 minutes (liquor ratio: 15 times), and washed in water for 1 minute. Thereafter, the moisture contained in the bundle was wiped off with a KIMTOWEL.

Next, 5 g of a commercially available hair coloring with acid dye A was applied to the bundle and kept at 50° C. for 20 minutes, washed in water for 1 minute, and thereafter sufficiently dried, to obtain a colored bundle of hair.

The obtained colored bundle was measured using the spectrocolorimeter, and a color difference (ΔE) between the colored bundle of hair and the uncolored bundle of hair was calculated. Thereafter, the coloring ability was evaluated.

It is indicated that the larger the ΔE is, the better the coloring ability becomes.

TABLE 6

| | | Pretreatment Agent for Acidic Hair Dye | | | | | Physical Properties | | |
| | | (% by weight) | | | | | Coloring | Color | |
| | Bleaching Treatment | SP-006 | P-1000 | QUARTAMIN 86W | Urea | MP | Distilled Water | Ability ($\Delta E$) | Fastness ($\Delta E$) | Squeakiness |
|---|---|---|---|---|---|---|---|---|---|---|
| Ex. No. | | | | | | | | | | |
| 27 | Not Used | 10 | 0 | 0 | 20 | 5 | 65 | 52.1 | 48.5 | ○ |
| 28 | Used | 10 | 0 | 0 | 20 | 5 | 65 | 62.1 | 58.2 | ○ |
| 29 | Not Used | 0 | 10 | 0 | 20 | 5 | 65 | 55.4 | 48.2 | ◎ |
| 30 | Used | 0 | 10 | 0 | 20 | 5 | 65 | 63.9 | 54.5 | ◎ |
| Comp. Ex. | | | | | | | | | | |
| 10 | Not Used | 0 | 0 | 0 | 0 | 0 | 0 | 48.4 | 43.2 | X |
| 11 | Used | 0 | 0 | 0 | 0 | 0 | 0 | 57.3 | 50 | X |
| 12 | Not Used | 0 | 0 | 20 | 20 | 5 | 65 | 48.6 | 45.4 | X |
| 13 | Used | 0 | 0 | 20 | 20 | 5 | 65 | 53.3 | 49.3 | X |

It can be seen from the results shown in Table 6 that the case where the treatment is carried out using the pretreatment agent for a hair coloring with acid dye containing PEI and urea (Examples 27 and 29) gives more excellent coloring ability and color fastness than the case where the treatment is carried out without pretreatment (Comparative Example 10) and shows no squeakiness during rinsing virgin hair.

The case where the treatment is carried out using the pretreatment agent for a hair coloring with acid dye containing PEI and urea (Examples 28 and 30) gives more excellent coloring ability than the case where the treatment is carried out without pretreatment (Comparative Example 11), and gives no squeakiness to damaged hair (subjected to bleaching treatment). Especially, the case where the treatment is carried out using the pretreatment agent for a hair coloring with acid dye containing PEI having a low molecular weight and urea (Example 30) gives more excellent color fastness to damaged hair than the case where the treatment is carried out without pretreatment (Comparative Example 11).

Also, it can be seen that the case where the treatment is carried out with the pretreatment agent for a hair coloring with acid dye containing stearyltrimethylammonium chloride and urea in place of PEI (Comparative Example 12) gives coloring ability and color fastness for virgin hair which are not so different from the case where the treatment is carried out without pretreatment (Comparative Example 10), and does not improve squeakiness during rinsing.

In addition, it can be seen that the case where the treatment is carried out using the pretreatment agent for a hair coloring with acid dye containing stearyltrimethylammonium chloride and urea in place of PEI (Comparative Example 13) gives coloring ability and color fastness for damaged hair worse than the case where the treatment is carried out without pretreatment (Comparative Example 11), and does not improve squeakiness during rinsing.

Example 31 and Comparative Example 14 and Reference Example 1

PEI (SP-003), urea and MP were dissolved in distilled water so as to have contents as shown in Table 7, to obtain a pretreatment agent for a hair coloring with acid dye.

As the physical properties for the obtained pretreatment agent, feeling, decoloring ability, coloring ability, color fastness and squeakiness (squeakiness during rinsing off the shampoo) were evaluated by the following methods. The results are shown in Table 7.

[Feeling]

A bundle of colored hair was dipped in the pretreatment agent as shown in Table 7 at 50° C. for 20 minutes (liquor ratio: 15 times), washed in water for 1 minute, and thereafter sufficiently dried. Sensory evaluation of feeling was made by five specialist panelists on the basis of the following evaluation criteria:

(Evaluation Criteria)

◎: Highly excellent (Four or five out of five judged that feeling was excellent).

○: Excellent (Three out of five judged that feeling was excellent).

Δ: Slightly poor (Two out of five judged that feeling was excellent).

X: Poor (Zero or one out of five judged that feeling was excellent).

[Decoloring Ability]

Two grams of a hair coloring with acid dye (manufactured by PIACELABO CORP., trade name: Hair Make Color RESHADE O30) was applied to 1 g of dried white human hair, and the hair was kept at room temperature for 10 minutes, thereafter washed in water for 1 minute and sufficiently dried, to obtain a bundle of colored hair.

Next, this bundle of colored hair was dipped in the pretreatment agent as shown in Table 7 at 50° C. for 20 minutes (liquor ratio: 15 times), washed in water for 1 minute and thereafter sufficiently dried to obtain a bundle of hair from which the dye was removed.

The color difference of the bundle of hair after removing dye ($\Delta E_1$) and the color difference of the bundle of hair before removing dye ($\Delta E_2$) were measured using a spectrocolorimeter (manufactured by Nippon Denshoku Kogyo K.K., trade name: SZ-Σ80, hereinafter referred to the same). Decoloring ability was evaluated in accordance with the following equation:

[Decoloring Ability]=[Color difference of bundle of hair ($\Delta E_2$) before removing dye]−[Color difference of the bundle of hair ($\Delta E_1$) after removing dye].

It is indicated that the larger the numerical value of decoloring ability is, the more excellent the decoloring ability becomes.

In addition, for the reference, the color difference ($\Delta E_1$) of a bundle of hair in which 1 g of dried white human hair before coloring, from which the dye was not removed, is also shown in Table 7 (Reference Example 1).

[Coloring Ability]

Two grams of a hair coloring with acid dye (manufactured by PIACELABO CORP., trade name: Hair Make Color RESHADE O30) was applied to the bundle of hair from which the dye was removed as described above (Example 31 and Comparative Example 14) and the bundle of hair from which the dye was not removed (Reference Example 1), and the hair was kept at 50° C. for 20 minutes. Thereafter, the hair was washed in water for 1 minute and sufficiently dried, to obtain a bundle of colored hair.

The color difference ($\Delta E_3$) of the obtained colored bundle was measured using a spectrocolorimeter (manufactured by Nippon Denshoku Kogyo K.K., trade name: SZ-Σ80, hereinafter referred to the same).

It is indicated the larger the color difference ($\Delta E_3$) of the colored bundle is, the more excellent the coloring ability becomes.

both bundles of colored hair is on the same level, the smaller the degree of elution of dye is, the more excellent the color fastness is.

[Squeakiness During Rinsing Off Shampoo with Water]

Five specialist panelists had examined squeakiness during rinsing the bundle of hair obtained in the item of [Coloring Ability] in Example 31 and Reference Example 1 with water by using a treatment solution [10% by weight aqueous solution of sodium polyoxyethylene(number of moles of oxyethylene added: 3) lauryl ether sulfate (manufactured by Kao Corporation, trade name: EMAL 20C)] on the basis of the following evaluation criteria.

(Evaluation Criteria)

⊚: Highly excellent (Four or five out of five evaluated that there was no squeakiness).

○: Excellent (Three out of five evaluated that there was no squeakiness).

Δ: Slightly wrong (Two out of five evaluated that there was no squeakiness).

X: Wrong (Zero or one out of five evaluated that there was no squeakiness).

TABLE 7

| | Components of Pretreatment Agent (% by weight) | | | | Decoloring Ability | | | Physical Properties | | | | |
|---|---|---|---|---|---|---|---|---|---|---|---|---|
| | | | | | | | | | | Color Fastness | | |
| | | | | | | | | Coloring | | Degree of Elution | | |
| | SP-003 | Urea | MP | Distilled Water | $\Delta E_2$ | $\Delta E_1$ | Decoloring Ability | Ability $\Delta E_3$ | $\Delta E_4$ | Of Dye ($A_{487}$) | Feeling | Squeakiness |
| Ex. No. 31 | 10 | 20 | 5 | 65 | 34.88 | 2.61 | 32.27 | 44.8 | 42.7 | 0.14 | ⊚ | ⊚ |
| Comp. Ex. 14 | 0 | 0 | 5 | 95 | 34.46 | 27.86 | 6.6 | — | — | — | X | X |
| Ref. Ex. 1 | — | — | — | — | — | 2.6*[1] | — | 41.1 | 37.7 | 0.13 | X | X |

(Note)
*[1] The value for the bundle of hair not subjected to coloring and decoloring treatments.

[Color Fastness]

As to Example 31 and Reference Example 1, the bundle of colored hair obtained in the term of [Coloring Ability] mentioned above was dipped in a 10% by weight aqueous solution of sodium polyoxyethylene(3E.O.) lauryl ether sulfate (manufactured by Kao Corporation, trade name: EMAL 20C) at 40° C. for 3 hours (ratio of hair: solution=1:15).

This bundle of colored hair was washed in water for 1 minute, and dried at room temperature. Thereafter, the color difference ($\Delta E_4$) of the bundle of hair after the above-mentioned treatment was obtained.

The smaller the difference between the color difference ($\Delta E_3$) of the bundle of colored hair and the color difference ($\Delta E_4$) of the bundle of hair after the above-mentioned treatment is, the more excellent the color fastness is.

On the other hand, the dye has been eluted from the bundle of colored hair into the treatment solution after the above-mentioned treatment. Accordingly, in order to examine the degree of elution of the dye, the elution of the dye (dye concentration eluted in the solution, absorbance at a wavelength of 487 nm) of a solution prepared by diluting the treatment solution 30 times. When the coloring ability of It can be seen from the results shown in Table 7 that the hair treated with the pretreatment agent containing PEI (Example 31) is more excellent in decoloring ability and feeling than the hair treated the pretreatment agent which does not contain PEI (Comparative Example 14), and shows little squeakiness (squeakiness during rinsing shampoo).

Also, the hair being colored after the treatment with the pretreatment agent containing PEI (Example 31) is more excellent in coloring ability and color fastness than the hair not subjected to dye-eliminating treatment (Reference Example 1).

Prescription Example 1

Preparation of Gel-Type Pretreatment Agent for Hair Coloring with Acid Dye

A gel-type pretreatment agent for a hair coloring with acid dye was prepared by mixing the following ingredients.

| (Ingredients) | (% by weight) |
|---|---|
| PEI | 10 |
| Urea | 20 |
| Benzyl Alcohol | 5 |
| Ethanol | 20 |
| Xanthan Gum | 1 |
| Perfume | Proper Amount |
| Purified Water | Bal. |

Prescription Example 2

Preparation of Liquid-Type Pretreatment Agent for Hair Coloring with Acid Dye

A liquid-type pretreatment agent for a hair coloring with acid dye was prepared by mixing the following ingredients.

| (Ingredients) | (% by weight) |
|---|---|
| PEI | 10 |
| Urea | 20 |
| Benzyl Alcohol | 5 |
| Ethanol | 20 |
| Perfume | Proper Amount |
| Purified Water | Bal. |

Prescription Example 3

Preparation of Hair Cream-Type Pretreatment Agent for Hair Coloring with Acid Dye A hair cream-type pretreatment agent for a hair coloring with acid dye was prepared by mixing the following ingredients.

| (Ingredients) | (% by weight) |
|---|---|
| Liquid Paraffin | 15 |
| Vaseline | 15 |
| White Beeswax | 2 |
| Anticorrosive Agent | Proper Amount |
| Perfume | Proper Amount |
| PEI | 5 |
| Urea | 20 |
| Xanthan Gum | 0.1 |
| Polyoxyethylene Cured Castor Oil | 3 |
| Purified Water | Bal. |

INDUSTRIAL APPLICABILITY

The pretreatment agent for a hair coloring with acid dye of the present invention exhibits some effects such that the pretreatment agent improves coloring ability and color fastness of a hair coloring with acid dye.

The invention claimed is:

1. A method of coloring hair comprising:
    (a) pretreating hair with a pretreatment agent comprising polyethyleneimine or a derivative thereof and urea, wherein the content of urea in the pretreatment agent is 0.1 to 60% by weight; and
    (b) coloring said pretreated hair with a composition comprising an acid dye.

2. The method for hair coloring with acid dye according to claim 1, wherein the content of the polyethyleneimine or in a derivative thereof is 0.01 to 30% by weight.

3. The method for hair coloring with acid dye according to claim 1 or 2, wherein the number-average molecular weight of the polyethyleneimine or a derivative thereof is 300 to 500000.

4. The method for hair coloring with acid dye according to claim 1, further comprising a step of washing the hair after the pretreating step and before the hair coloring step.

* * * * *